US011896582B2

(12) United States Patent
Clarence-Smith

(10) Patent No.: US 11,896,582 B2
(45) Date of Patent: *Feb. 13, 2024

(54) USE AND COMPOSITION FOR TREATING MYASTHENIA GRAVIS AND OTHER MYASTHENIC SYNDROMES

(71) Applicant: DAS-MG, INC., Boston, MA (US)

(72) Inventor: Kathleen E. Clarence-Smith, Washington, DC (US)

(73) Assignee: DAS-MG, INC., Boston, MA (US)

( * ) Notice: Subject to any disclaimer, the term of this patent is extended or adjusted under 35 U.S.C. 154(b) by 316 days.

This patent is subject to a terminal disclaimer.

(21) Appl. No.: 17/085,964

(22) Filed: Oct. 30, 2020

(65) Prior Publication Data

US 2021/0046053 A1  Feb. 18, 2021

Related U.S. Application Data

(63) Continuation of application No. 16/697,240, filed on Nov. 27, 2019, now Pat. No. 10,842,778, which is a continuation of application No. 16/476,460, filed as application No. PCT/US2018/012754 on Jan. 8, 2018, now abandoned.

(60) Provisional application No. 62/443,904, filed on Jan. 9, 2017.

(51) Int. Cl.
*A61K 31/4178* (2006.01)
*A61P 21/04* (2006.01)
*A61K 31/4425* (2006.01)

(52) U.S. Cl.
CPC ...... *A61K 31/4178* (2013.01); *A61K 31/4425* (2013.01); *A61P 21/04* (2018.01)

(58) Field of Classification Search
CPC .. A61K 31/4178; A61K 31/4425; A61P 21/04
See application file for complete search history.

(56) References Cited

U.S. PATENT DOCUMENTS

| 4,042,698 | A | 8/1977 | Zappia |
| 7,456,154 | B2 | 11/2008 | Soreq |
| 9,782,397 | B2 | 10/2017 | Ferrari |
| 10,842,778 | B2 | 11/2020 | Clarence-Smith |
| 2002/0051815 | A1 | 5/2002 | Rubin et al. |
| 2007/0049576 | A1 | 3/2007 | Barlow |
| 2009/0209459 | A1 | 8/2009 | Hamer |
| 2009/0264388 | A1 | 10/2009 | Maghni |
| 2011/0071135 | A1 | 3/2011 | Chase et al. |
| 2011/0243924 | A1 | 10/2011 | Supervia |
| 2013/0116215 | A1 | 5/2013 | Coma |
| 2014/0335021 | A1 | 11/2014 | Salih |
| 2015/0231122 | A1 | 8/2015 | Clarence-Smith |

FOREIGN PATENT DOCUMENTS

| CN | 102258492 | 11/2011 |
| CN | 102552381 | 7/2012 |
| CN | 105434403 | 3/2016 |
| EP | 0431443 | 12/1991 |
| EP | 3589369 | 1/2020 |
| GB | 2327348 A | 1/1999 |
| JP | S56104814 | 8/1981 |
| WO | WO 95/31194 | 11/1995 |
| WO | 2006005017 | 1/2006 |
| WO | WO 2018/129434 | 7/2018 |
| WO | WO 2018140412 | 8/2018 |

OTHER PUBLICATIONS

Zofran, (Zofran Product Information Version 5.0, GlaxoSmithKline, Sep. 24, 2012, pp. 1-16) Year 2012.
Gold et al (Therapeutic Advances in Neurological Disorders, 2008; 1 (2):99-114.
Mulvenna, "Subcutaneous Ondansetron", The Lancet; Apr. 25, 1992; 339, 8800, p. 1059.
Macario., et al., "Improved Outcome with Chronic Subcutaneous Infusion of Ondansetron for Intractable Nausea and Vomiting", Anesthesia & Analgesia: Jul. 1996—vol. 83, Issue 1, p. 194-195.
Bird, Treatment of myasthenia gravis, UpToDate, Dec. 7, 2016 [retrieved on Nov. 25, 2019 ] Retrieved from URL: https://web.archive.org/web/20161204141047.
Capacio, et al, "Interaction of Pyridostigmine with the 5-HT3 Receptor Antagonist Ondansetron in Guinea Pigs", Proceedings of the Medical Defense BioScience Review, col. 2, May 13, 1993.
International Search Report for PCT/US2018/012754 dated Mar. 9, 2018.
Abicht A, Muller J S, Lochmiiller H. Congenital Myasthenic Syndromes. In: Pagon RA, Adam MP, Ardinger HH, Wallace SE, Amemiya A, Bean LJH, Bird TD, Ledbetter N, Mefford HC, Smith RJH, Stephens K, editors. GeneReviews®[Internet]. Seattle (WA): University of Washington, Seattle; 1993-2016. May 9, 2003 [updated Jul. 14, 2016].
Cho J-R et al 2016: Cho J-R, Duong AV, Nguyen LTT, Chi S-C. "Design of transdermal matrix patch containing ondansetron". J Pharm Investigation. 2016 46(7): 677-684—Abstract Only.
Drachman DB. Myasthenia Gravis. Semin Neurol. 2016; 36:419-424. Epub Sep. 23, 2016.
Engel AG. Congenital Myasthenic Syndromes in 2012. Curr. Neurol Neurosci Rep, 2012; 12:92-101.

(Continued)

*Primary Examiner* — Kevin E Weddington
(74) *Attorney, Agent, or Firm* — Transformative Legal LLC; Len S. Smith; Julie E. Kurzrok

(57) ABSTRACT

The present invention provides a new compositions and methods to enable the safe administration of pyridostigmine to mammalian subjects, including those with myasthenic syndromes including Myasthenia Gravis, with said compositions comprising combinations, including fixed-dose combinations, of an antagonist of the 5-hydroxytryptamine subtype-3 receptor ("5HT3-antagonist") with an effective dose of pyridostigmine. The compositions and methods of the present invention provide for an increase in the tolerable dose of pyridostigmine over that of pyridostigmine when administered alone.

5 Claims, No Drawings

(56) References Cited

OTHER PUBLICATIONS

Gotterer L, Li Y. Maintenance immunosuppression in myasthenia gravis. J Neurol 20 Sci. 2016; 369:294-302. Epub Aug. 28, 2016.
Howard J.F. Clinical Overview of MG. Myasthenia Gravis Foundation of America; 2015.
Koland JVI et al. 2010: Koland M, Sandeep VP. Charyulu NR. Ondansetron Hydrochloride: Effect of Additives on in vitro Drug Release and Mucosal Permeation. J Young Pharmacists. 2010, 2(3):216-222.
O'Grady GL, Verschuuren C, Yuen M, Webster R, Menezes M, Fock JM, Pride N, Best HA, Benavides Damm T, Turner C, Lek M, Engel AG, North KN, Clarke NF, MacArthur DG, Kamsteeg EJ, Cooper ST. Variants in SLC18A3, vesicular acetylcholine transporter, cause congenital myasthenic syndrome. Neurology. 2016; 87:1442-1448. Epub Sep. 2, 2016.
Phillips WDI, Vincent A2. Pathogenesis of myasthenia gravis: update on disease types, models, and mechanisms. FI000Res. 2016; 27:5.
Shelton GDI. Myasthenia gravis and congenital myasthenic syndromes in dogs and cats: A history and mini-review. Neuromuscul Disord. 2016; 26: 331-334. Epub Mar. 10, 2016.
Smith SV, Lee AG. Update on Ocular Myasthenia Gravis. Neurol Clin. 2017; 35:115-123.
JHEE Standford et al: "Centrally Acting Antiemetics Mitigate Nausea and Vomiting in Patents with Alzheimer's Disease who receive Revastigmine", Clinical Neuropharmacoloty, vol. 25, No. 2, Mar. 2002, pp. 122-123—EP Search Report.
Christina VT NG: "Myasthenia gravis and a rare Complication of Chemotherapy", Medical Journal of Australia, vol. 182, No. 3, Feb. 7, 2005, p. 120—EP Search Report.
Drachman, et al "Treatment of Refractory Myasthenia: Rebooting with High-Dose Cyclophosphamide", Animals of Neurology, vol. 53, No. 1, Jan. 1, 2003, pp. 29-34—EP Search Report.
Dezern, et al, "Repeated treatment with high dose cyclophosphamide for severe autoimmune diseases", American Journal of Blood Research, vol. 3, No. 1, Jan. 2013, pp. 84-90—EP Search Report.
Nagappa et al, "Long-term efficacy and limitation of cyclophosphamide in myasthenia gravis", Journal of Clinical Neuroscience, vol. 21, No. 11, Nov. 2014, pp. 1909-1914—EP Search Report.
Kamel, et al, "The caustious use of cyclizine in a patient with Myasthenia Gravis", Journal of palliative medicine, vol. 12, No. 10, Oct. 6, 2009, pp. 879-880—EP Search Report.
Chase, Thomas, et al, "High-dose cholinesterase inhibitor treatment of Alzhimer's disease", Alzheimer's & Dementia: The Journal of the Alzheimer's Association, vol. 11, No. 7, Jul. 1, 2015—EP Search Report.
Myasthenia Gravis Fact Sheet; National Institute of neurological Discorders and Stroke, 2016.
Lexell, "Evidence for Nervous System Degeneration with Advancing Age", Lund University Hospital, 1997 American Society for Nutritional Sciences, pp. 1011S-1013S.
Makarious et al., "Myasthenia gravis: An Emerging Toxicity of Immune Checkpoint Inhibitors", European Journal of Cancer 82(2017) 128-136, Jun. 27, 2017.
Treatment of Myasthenia Gravis, UpToDate, Dec. 7, 2016, (retrieved on Feb. 15, 2018) Retrieved from URL: https://web.archive.org/web/20161204141047.
Pohanka, "Inhibitors of Acetylocholinesterase and Bolyrylcholinesterase Meet Immunity", International Journal of Molecular Sciences: 2014, 15, 9809-9825; doi: 10.3390/ijms15069809.
European Extended Search Report dated Feb. 19, 2020 for EP18735807.2.
European response to Extended Search Report dated Aug. 26, 2020 for EP18735807.2.
Bangalor et al. "Fixed-dose combinations improve medication complicance: a meta-analysis." Aug. 1, 2007, pp. 1-5. Bangalore Sripal.
Bingle et al. "Continuous subcutaneous neostigmine in the management of severe myasthenia gravis." (British Medical Journal, Apr. 21, 1979; 1(6170): 1050. Bingle James P.
Bloxiverz Prescribing Information, revised May 1, 2013. Bloxiverz Information.
Canadian Office Action dated Feb. 4, 2021 for CA3071377. Canadian Office Action.
Couturier. "Autoimmune myasthenia gravis in a ferret." Journal of the American Veterinary Medical Association Nov. 1, 2009, 235(12), 1462-6. Couturier Jerome.
Gavini et al. "Formulation and Characterization of Controlled Release Bioadhesive Nanoparticles Encapsulated with Neostigmine Bromide." IJPSR, Aug. 1, 2015; vol. 6(8): 3501-3510. Gavini Venkatesh.
Gillies, J.D. "Effects of Neostigmine and Pyridostigmine at the Neuromuscular Junction." Proceedings of the Australian Association of Neurologists, Jan. 1, 1978, vol. 14 (Clin. Exp. Neurol. 1977), p. 271-279. Gillies John D.
Hermann et al. "Myasthenia Gravis and the Myasthenic Syndrome." California Medicine, Sep. 1, 1970, vol. 113, pp. 27-36. Hermann Christian Jr.
International Search Report dated Apr. 23, 2018 for PCT/US2018/14901. International Search Report.
International Search Report dated Oct. 2, 2018 for PCT/US2018/43391. International Search Report.
International Search Report dated Oct. 15, 2018 for PCT/US2018/43636. International Search Report.
Langford et al. "Fosaprepitant and aprepitant: an update of the evidence for their place in the prevention of chemotherapy induced nausea and vomiting." Core Evidence, Sep. 24, 2009. vol. 5, pp. 77-90. Langford Patrick.
Maggi et al. "Treatment of Myasthenia Gravis." Clin Drug Investig, Oct. 1, 2011; 31(10): 691-701 (Year: 2011). Maggi Lorenzo.
Mestinon Data Sheet. Wayback Machine publicly available date: Oct. 13, 2012. Retrieved from the internet <URL: https://web.archive.org/web/20121013115507/https://www.medsafe.govt.nz/profs/datasheet/m/Mestinontab.pdf>; pp. 1-5 (Year:2012). Mestinon Data Sheet.
Non-Final Office Action dated Mar. 31, 2022 for U.S. Appl. No. 16/752,590. Phan Doan Thi-Thuc.
Final Office Action dated Nov. 10, 2022 for U.S. Appl. No. 16/752,590. Doan Thi-Thuc.
Non-Final Office Action dated Aug. 18, 2020 for U.S. Appl. No. 16/480,177. Rodriguez Tayna B.
Final Office Action dated Feb. 10, 2021 for U.S. Appl. No. 16/480,177. Rodriguez Rayna B.
Non-Final Office Action dated Mar. 20, 2023 for U.S. Appl. No. 17/316,643. Rodrigueza Rayna B.
Rouet et al. "Nifedipine Blocks Ondansetron Electrophysiological Effects in Rabbit Purkinje Fibers and Decreases Early Afterdepolarization Incidence." Current Clinical Pharmacology, Feb. 1, 2012, 7, 41-18. Rouet Rene.
Stewart et al. "Stability of Ondansetron Hydrochloride and 12 Medications in Plastic Syringes." Am J Health Syst Pharm, vol. 55, Dec. 15, 1998. 24; 2630-2634. Abstract Only. Stewart James T.
Non-Final Office Action dated May 27, 2020 for U.S. Appl. No. 16/697,240. Weddington Kevin E.
West. "Solid State Chemistry and its Applications." John Wiley & Sons, 1984. Feb. 1, 1985, West Anthony R.
Wolff. "Burger's Medicinal Chemistry and Drug Discovery." ImmunoPharmaceutics, Inc. San Diego California. Fifth Edition, vol. 1: Principles and Practice. John Wiley & Sons, New York, Jan. 1, 1997. pp. 975-977. Wolff Manfred E.

USE AND COMPOSITION FOR TREATING MYASTHENIA GRAVIS AND OTHER MYASTHENIC SYNDROMES

RELATED APPLICATIONS

This application is a continuation of U.S. patent application Ser. No. 16/697,240, filed Nov. 27, 2019, which is a continuation of U.S. patent application Ser. No. 16/476,460, filed Jul. 8, 2019, which is a national stage application of PCT International Application No. PCT/US2018/012754, which was filed Jan. 8, 2018, claiming the benefit of U.S. Provisional Patent Application Ser. No. 62/443,904, filed Jan. 9, 2017, the disclosure for all of which is incorporated herein in their entirety by reference.

FIELD OF THE INVENTION

This invention pertains to the field of the treatment of the symptoms of muscle weakness associated with myasthenia gravis (MG) and other myasthenic syndromes in mammalian subjects, particularly including humans, dogs, and cats suffering from these diseases.

OBJECT OF THE INVENTION

The present invention provides a new composition and method to enable the safe administration of pyridostigmine to mammalian subjects with myasthenic syndromes, including MG, with said composition comprising combinations, including fixed-dose combinations, of an antagonist of the 5-hydroxytryptamine subtype-3 receptor ("5HT3-antagonist") with an effective dose of pyridostigmine.

BACKGROUND OF THE INVENTION

Myasthenia gravis (MG) is a chronic autoimmune disease of the neuromuscular junction (NMJ) caused by antibodies that attack components of the postsynaptic membrane, impair neuromuscular transmission, and lead to varying degrees of weakness and fatigue of skeletal muscle. The prevalence of MG in the United States is estimated at 14 to 20 per 100,000 population, with approximately 36,000 to 60,000 cases in the United States (Howard, 2015). However, MG remains underdiagnosed and the prevalence is probably higher. The disease has also been described in dogs, and cats (Shelton, 2016).

The hallmark of the disease is muscle weakness that increases during periods of activity and improves after periods of rest. Muscular weakness can be generalized or localized to certain muscle groups, and involvement of the bulbar and respiratory muscles can be life threatening (Phillips and Vincent, 2016). Groups of muscles are often involved in typical patterns. Certain muscles such as those that control eye and eyelid movement, facial expression, chewing, talking, and swallowing are often, but not always, involved in the disorder. The muscles that control breathing and neck and limb movements may also be affected.

MG occurs in all ethnic groups and in both genders. It most commonly affects young adult women (under 40) and older men (over 60), but it can occur at any age (Myasthenia Gravis Fact Sheet; National Institute of neurological Disorders and Stroke, 2016). In neonatal myasthenia, the fetus may acquire immune proteins (antibodies) from a mother affected with MG. Generally, cases of neonatal MG are temporary and the child's symptoms usually disappear within 2-3 months after birth (Myasthenia Gravis Fact Sheet; National Institute of neurological Disorders and Stroke, 2016). Other children develop MG that is indistinguishable from occurrences in adults. MG in juveniles is uncommon (Myasthenia Gravis Fact Sheet; National Institute of neurological Disorders and Stroke, 2016).

The basic abnormality in MG is a reduction in nicotinic acetylcholine receptors (AChRs) at neuromuscular junctions due to the effects of autoantibodies that are directed against the AChRs in most patients, or against neighboring proteins involved in the clustering of AChRs, such as MuSK, LRP-4, or agrin (Drachman, 2016).

The diagnosis may be missed during the early stages of the disease, and depends on the recognition of clinical manifestations, the measurement of autoantibodies, and/or electrophysiological features (Drachman, 2016).

Rarely, children may show signs of congenital myasthenia or congenital myasthenic syndrome (CMS). These are not autoimmune disorders, but are caused by defective genes that produce abnormal proteins instead of those that normally are involved in cholinergic transmission: acetylcholinesterase (the enzyme that breaks down acetylcholine), acetylcholine receptors, and other proteins present along the muscle membrane (Engel, 2012).

In some rare cases, a myasthenic syndrome is due to bi-allelic variants in the gene encoding the vesicular acetylcholine transporter (VAChT) located in the presynaptic terminal (O'Grady et al, 2016). In other cases, degeneration of the nerves that innervate muscles such as occurs with aging (Lexel, 1997) leads to a myasthenic syndrome. Recently (Makarious et al, 2017), have reported on a myasthenic syndrome involving an emerging toxicity of checkpoint inhibitors used for the treatment of certain malignancies. Most individuals with CMS, or with an immune-oncology therapy-related myasthenic syndrome, or with progressive age related degeneration of the motor neurons that innervate muscles benefit from the same treatment as those that are effective in patients with autoimmune MG, namely choline esterase (ChE) inhibitors (Engel 2012; Abicht et al, 2003 updated in 2014).

Ocular myasthenia gravis (OMG) is a localized form of MG in which autoantibodies directed against acetylcholine receptors block or destroy these receptors at the postsynaptic neuromuscular junction. The hallmark of OMG is a history of painless weakness or fatigability of the extraocular muscles and ptosis with normal pupillary function and visual acuity. Clinical, laboratory, electrophysiologic, and pharmacologic tests are available for diagnosis. Treatment can begin with symptom management; there is no cure (Smith and Lee, 2017).

The treatment of myasthenic syndromes involves treatment of the symptoms through the enhancement of cholinergic transmission at the neuromuscular junction by Choline Esterase Inhibitors (ChEIs) that do not appreciably cross the Blood-Brain-Barrier (BBB), such as pyridostigmine. Patients with autoimmune-related myasthenic syndromes may also benefit from immunotherapy to slow disease progression. Options for immunosuppression include corticosteroids, azathioprine, mycophenolate mofetil, cyclosporine, tacrolimus, methotrexate, rituximab, cyclophosphamide, intravenous immunoglobulin, plasmapheresis, and thymectomy (Gotterer and Li, 2016).

Pyridostigmine treats the symptoms by retarding the enzymatic hydrolysis of acetylcholine at cholinergic synapses, so that acetylcholine concentrations increase at the neuromuscular junction and the effect of acetylcholine is both increased and prolonged. Cholinesterase inhibitors have been shown to cause considerable improvement in some patients with MG and little to none in others (Howard, 2015). Strength rarely returns to normal, possibly because of dose-limiting adverse events (diarrhea, nausea, vomiting) that preclude the use of fully effective doses of pyridostigmine. Pyridostigmine bromide (Mestinon), which does not appreciably cross the BBB, is commonly used for the treatment of MG. No fixed dosage schedule suits all patients. The need for pyridostigmine varies from day-to-day and during the same day in response to infection, menstruation, emotional stress, and hot weather. Adverse effects of pyridostigmine typically consist of gastrointestinal complaints, queasiness, loose stools, nausea, vomiting, abdominal cramps, and diarrhea (Howard, 2015). Increased bronchial and oral secretions are a serious problem in patients with swallowing or respiratory insufficiency. Central nervous system side effects are rare with pyridostigmine.

Gastro-intestinal side effects are an important source of discomfort for the patient, may be a source of non-compliance, may preclude the use of fully effective doses, or may result in the need to decrease the dose of pyridostigmine to mitigate these side effects whereupon these side effects become dose-limiting. As a consequence, efficacy is reduced.

Thus, the problem of providing safe, chronic treatment of MG and other myasthenic syndromes with pyridostigmine therapeutic or even at higher maximally effective doses remains unsolved.

Definitions

"MG": Myasthenia Gravis. MG is a chronic neuromuscular autoimmune disease, characterized by muscle weakness. The basic abnormality in MG is a reduction in the number or function of acetylcholine nicotinic receptors (AChRs) at neuromuscular junctions due to the effects of autoantibodies. About 85% of patients with generalized MG have antibodies to AChRs. Antibodies to other proteins at the neuromuscular junction are present in some cases of MG, such as antibodies to muscle-specific kinase, or to low density lipo-protein 4, or to agrin.

"Myasthenic syndrome": refers to conditions associated with muscle weakness in which the cholinergic transmission at the neuromuscular junction is decreased either because of a decrease in the number and/or dysfunction of post-synaptic nicotinic receptors or to a decrease in the amount of acetylcholine ("ACh") available at the neuromuscular junction due to gene mutations in the presynaptic proteins involved in the synthesis, storage and release of ACh, or to degeneration of cholinergic nerves that innervate muscles. An emerging myasthenic syndrome (with or without auto antibodies to nicotinic receptors) has been reported in association with immune-therapies used for the treatment of certain malignancies. Myasthenic syndromes are sometimes loosely referred to as MG in the medical literature but herein, all MG-like conditions which do not involve autoantibodies to nicotinic receptors will be referred to as myasthenic syndromes. MG itself is a myasthenic syndrome and is considered as such herein, although, as the most prominent myasthenic syndrome it is often mentioned specifically (as in the phrase "MG and other myasthenic syndromes").

"Effective dose of 5HT3-antagonist": this expression, as used herein, refers to a single dose of said 5HT3-antagonist that is at least as high as the dose preventing or treating nausea and vomiting in a mammalian subject. Said single dose is from 1 mcg to 300 mg, normally from 0.01 mg/kg to 1.8 mg/kg of body weight.

"Effective daily dose of 5HT3-antagonist": this expression, as used herein, refers to a daily dose of said 5HT3-antagonist that is at least as high as the dose preventing or treating nausea and vomiting in pediatric or adult human patients undergoing cancer chemotherapy, said effective daily dose being from 0.03 mg/kg to 3 mg/kg of body weight.

"Pyridostigmine": unless otherwise specified, this term, as used herein, refers to a pharmaceutically acceptable salt of pyridostigmine ("pyridostigmine pharmaceutically acceptable salt"), the daily doses and the amounts per unit form thereof being expressed as equivalents of pyridostigmine bromide.

"Effective daily dose of pyridostigmine": this expression, as used herein, refers to a pyridostigmine daily dose, including doses used in the titration period, equivalent to at least 0.5 mg/kg of body weight of pyridostigmine bromide.

"Fully effective (daily) dose", as used herein for pyridostigmine, refers to any pyridostigmine daily dose allowing the expression of full pyridostigmine efficacy, heretofore hindered by the typical pyridostigmine adverse effects.

"Effective amount per unit form", referring to pyridostigmine, is a pyridostigmine amount per unit form equivalent to at least 0.5 mg of pyridostigmine bromide.

"Mammal" or "mammalian subject" as used herein refer to any class of warm-blooded higher vertebrates (such as placentals, marsupials, or monotremes) that nourish their young with milk secreted by mammary glands, have the skin usually more or less covered with hair; and include, but are not limited to, a human, a dog, and a cat.

SUMMARY OF THE INVENTION

It has now been found that, by using a 5-HT3 receptor antagonist, also referred to as a 5-HT3 receptor inhibitor or simply a 5HT3-antagonist, in constant combination with pyridostigmine bromide, it is possible to treat mammalian subjects, and particularly humans, dogs, and cats, suffering from symptoms of muscle weakness associated with MG or another myasthenic syndrome by maintaining a therapeutically fully effective pyridostigmine bromide daily dose without any adverse effect.

In particular, the constant combination of a 5HT3-antagonist with pyridostigmine allows for the first time the enablement of the full efficacy of pyridostigmine in the treatment of symptoms of muscle weakness associated with MG and other myasthenic syndromes.

Thus, the present invention provides a method for treating symptoms of muscle weakness associated with MG and other myasthenic syndromes, which comprises administering to a mammalian subject in need of said treatment a combination of a 5HT3-antagonist with an effective daily dose of pyridostigmine.

Any of the 5HT3-antagonists disclosed in the literature may be used in combination with a dose of pyridostigmine that is generally at least as high as that of the pyridostigmine bromide currently recommended dose for treating MG, and even much higher. The chronic use of this combination mitigates or even eliminates the gastro-intestinal dose-limiting adverse effects of pyridostigmine, thus enabling the safe administration of the recommended or even higher than currently recommended dose of pyridostigmine bromide (fully effective dose), leading to greater efficacy and safety of pyridostigmine.

According to the present invention, preferably, the 5HT3-antagonists used are those shown to be effective for preventing or treating nausea and vomiting following cancer chemotherapy. In fact, surprisingly, 5-HT3 receptor inhibitors, known to block nausea, vomiting, and diarrhea induced by chemotherapeutic drugs, have been shown, in particular when administered at high doses, to also block the gastrointestinal side effects of pyridostigmine without affecting its efficacy in treating symptoms of muscle weakness associated with MG or other myasthenic syndromes, thus allowing the administration of pyridostigmine fully effective doses.

This finding is surprising also, given the apparently simple solution found by the present inventors, because, notwithstanding the gravity of the illness and the fact that both pyridostigmine and the 5HT3-antagonists were two families of products in use for more than twenty-thirty years, each in its own indication, to date nobody thought that, by combining an effective daily dose of 5HT3-antagonist with an effective daily dose of pyridostigmine, it would have been possible to safely improve the conditions of patients suffering from MG.

Thus, the present invention provides a method for treating symptoms of muscle weakness associated with MG and other myasthenic syndromes, which comprises administering to mammalian subjects, and in particular, humans, dogs, and cats, in need of said treatment an effective daily dose of a 5HT3-antagonist in combination with an effective daily dose of a pharmaceutically acceptable salt of pyridostigmine.

According to an embodiment, the invention provides a pharmaceutical combination comprising a 5HT3-antagonist, at a daily dose that is at least as high as the pediatric or adult dose shown to be effective for the prevention or treatment of chemotherapy-induced nausea and vomiting, and a fully effective dose of a pyridostigmine pharmaceutically acceptable salt.

According to another embodiment, the invention provides a 5HT3-antagonist, in a pharmaceutical composition comprising, as an active ingredient, said 5HT3-antagonist in an amount at least as high as the pediatric or adult dose shown to be effective for the prevention or treatment of chemotherapy-induced nausea and vomiting, in admixture with a pharmaceutical carrier, for use for preventing or attenuating the adverse effects of pyridostigmine in the treatment of symptoms of muscle weakness associated with MG and other myasthenic syndromes.

According to a further embodiment, the invention includes the use of a 5HT3-antagonist for the preparation of a medicament including a pharmaceutical composition comprising, as an active ingredient, said 5HT3-antagonist, in an amount per unit form at least as high as the pediatric or adult dose shown to be effective for the prevention or treatment of chemotherapy-induced nausea and vomiting (effective amount per unit form), in admixture with a pharmaceutical carrier, for preventing or curing the adverse effects of pyridostigmine in the treatment of symptoms of muscle weakness associated with MG and other myasthenic syndromes.

As set forth above, the amount per unit form of the 5HT3-antagonist is at least as high as the pediatric or adult dose shown to be effective for the prevention or treatment of chemotherapy-induced nausea and vomiting and may be up to 4 times said dose. In addition, said composition comprising said 5HT3-antagonist for the first time allows the administration of fully effective pyridostigmine doses to mammalian subjects suffering from symptoms of muscle weakness associated with MG or other myasthenic syndromes, with the consequent expression of the pyridostigmine full efficacy.

According to yet a further embodiment, the invention provides a pharmaceutical fixed-dose combination including a pharmaceutical composition in dosage unit form comprising a 5HT3-antagonist, in an amount per unit form that is at least as high as the pediatric or adult dose shown to be effective for the prevention and treatment of chemotherapy-induced nausea and vomiting, as Component (a), and an effective amount per unit form of pyridostigmine, as Component (b), in admixture with a pharmaceutical carrier or vehicle.

For the treatment of symptoms of muscle weakness associated with MG or other myasthenic disorders by oral route:
(a) the 5HT3-antagonist Component (a) of the combination is administered at a single dose of from 0.001 mg/kg to 1.8 mg/kg of body weight, given from one to three times per day, with a maximum of 300 mg/day; and
(b) the pyridostigmine Component (b) of the combination is administered at a single dose equivalent to from 0.5 mg/kg to 6 mg/kg of body weight given in unit forms comprising an amount per unit form equivalent to from 15 mg to 800 mg, said unit form being administered from three times per day to six times per day.

In the above combination, including fixed-dose combinations, the amount of pyridostigmine in an Immediate Release ("IR") unit form (amount per unit form) will range from 15 mg to 800 mg, normally from 30 mg to 800 mg, from 30 mg to 500 mg, from 30 mg to 400 mg, from 30 mg to 200 mg, from 30 mg to 180 mg, from 30 mg to 120 mg or from 30 mg to 90 mg, depending on safety and tolerability (per day the dose is from 180 mg to 2400 mg, and even more, normally from 180 mg to 1200 mg, from 180 mg to 1080 mg or from 180 mg to 720 mg). If the 5HT3-antagonist is ondansetron, the ondansetron amount per unit form in combination with pyridostigmine will range from 2 mg to 16 mg, normally from 2 mg to 8 mg or from 4 mg to 8 mg.

The dose of pyridostigmine in Extended Release ("ER") unit form will range from 90 mg to 800 mg, normally from 90 mg to 400 mg, from 90 mg to 360 mg or from 90 to 240 mg, to be administered 3-6 times per day. If the 5-HT3 antagonist is dolasetron, the dolasetron dose per unit form to be administered in combination with pyridostigmine will be equivalent to a range from 100 mg to 200 mg of dolasetron mesylate.

DETAILED DESCRIPTION

The present invention provides, according to its aspects:
(a) a method for safely improving the conditions or symptoms of muscle weakness associated with of mammalian subjects, and particularly, humans, dogs, and cats, suffering from MG or other myasthenic syndromes by treating said subjects with a 5HT3-antagonist in combination with pyridostigmine;
(b) a 5HT3-antagonist, for use in the treatment of MG and other myasthenic syndromes in combination with pyridostigmine;
(c) the use of a 5HT3-antagonist for the preparation of a medicament for the treatment of symptoms of muscle weakness associated with MG and other myasthenic syndromes in combination with pyridostigmine; and
(d) a fixed-dose combination consisting of a pharmaceutical composition in dosage unit form comprising, as active ingredients, a 5HT3-antagonist Component (a) and pyridostigmine Component (b).

The 5HT3-Antagonist

Any 5HT3-antagonist may be used for allowing the safe treatment of MG and other myasthenic syndromes with normal, but also with high and very high, fully effective pyridostigmine doses. Antagonists of the 5HT3 receptor that are shown to be effective for the prevention or treatment of chemotherapy-induced nausea and vomiting are particularly useful according to the present invention.

The 5HT3-antagonist is preferably selected from the group consisting of 5-methyl-2-[(4-methyl-1H-imidazol-5-yl)methyl]-2,3,4,5-tetrahydro-1H-pyrido[4,3-b]indol-1-one (alosetron) and pharmaceutically acceptable salts and solvates thereof, especially its hydrochloride, disclosed in U.S. Pat. No. 5,360,800; (±)-6-chloro,3,4-dihydro-4-methyl-3-oxo-N-(quinuclidinyl)-2H-1,4-benzoxazine-8-carboxamide (azasetron) and pharmaceutically acceptable salts and solvates thereof, especially its hydrochloride, disclosed in U.S. Pat. No. 4,892,872; [(1S,5R)-8-methyl-8-azabicyclo[3.2.1]octan-3-yl]3,5-dichlorobenzoate (bemesetron, CAS: 40796-97-2); (10R)-10-[(2-methyl-1H-imidazol-1-yl) methyl]-5,6,9,10-tetrahydro-4H-pyrido(3,2,1-jk) carbazol-11-one (cilansetron) and pharmaceutically acceptable salts and solvates thereof, especially its hydrochloride monohydrate, disclosed in U.S. Pat. No. 4,939,136; (3R)-10-oxo-8-azatricyclo[5.3.1.0$^{3,8}$]undec-5-yl 1H-indole-3-carboxylate (dolasetron) and pharmaceutically acceptable salts and solvates thereof, especially its monomethanesulfonate monohydrate, disclosed in U.S. Pat. No. 4,906,755; (+)-(R)-8,9-dihydro-10-methyl-7-[(5-methylimidazol-4-yl)methyl]pyrido[1,2-a]indol-6(7H)-one (fabesetron) and pharmaceutically acceptable salts and solvates thereof, especially its hydrochloride or maleate, disclosed in U.S. Pat. No. 5,141,945; 1-methyl-N-((1R,3r,5S)-9-methyl-9-azabicyclo[3.3.1]nonan-3-yl)-1H-indazole-3-carboxamide (granisetron) and pharmaceutically acceptable salts and solvates thereof, especially its hydrochloride, disclosed in U.S. Pat. No. 4,886,808; 2,3-dihydro-N-(8-methyl-8-azabicyclo[3.2.1]oct-3-yl)-2-oxo-1H-benzimidazole-1-carboxamide (itasetron) and pharmaceutically acceptable salts and solvates thereof, especially its hydrochloride, disclosed in U.S. Pat. No. 5,223,511; 1-phenylmethyl-2-(1-piperazinyl)-1H-benzimidazole (lerisetron) and pharmaceutically acceptable salts and solvates thereof, specially its hydrochloride, disclosed in U.S. Pat. No. 5,256,665 and, in a transdermal preparation, in U.S. Pat. No. 6,136,807; 6-fluoro-5-methyl-2-[(5-methyl-1H-imidazol-4-yl)methyl]-2,3,4,5-tetrahydro-1H-pyrido[4,3-b]indol-1-one (lurosetron, CAS 128486-54-4) and pharmaceutically acceptable salts and solvates thereof, especially its mesylate (GR 87442 N); (±) 1,2,3,9-tetrahydro-9-methyl-3-[(2-methyl-1H-imidazol-1-yl)methyl]-4H-carbazol-4-one (ondansetron) and pharmaceutically acceptable salts and solvates thereof, especially its hydrochloride dihydrate, disclosed in U.S. Pat. No. 4,695,578; (3aS)-2-[(S)-1-azabicyclo[2.2.2]oct-3-yl]-2,3,3a,4,5,6-hexahydro-1-oxo-1H-benz[de]isoquinoline (palonosetron) and pharmaceutically acceptable salts and solvates thereof, especially its hydrochloride, disclosed in U.S. Pat. No. 5,202,333; 1-methylindol-3-yl)-[(5R)-4,5,6,7-tetrahydro-3H-benzimidazol-5-yl]methanone (ramosetron) and pharmaceutically acceptable salts and solvates thereof, especially its fumarate, disclosed in U.S. Pat. No. 5,344,927; endo-N-(8-methyl-8-azabicyclo[3.2.1]oct-3-yl)-2,3-dihydro-3,3-dimethyl-indole-1-carboxamide (3,3-dimethyl-N-1αH,5αH-tropan-3α-yl-1-indolinecarboxamide, ricasetron, CAS 117086-68-7) and pharmaceutically acceptable salts and solvates thereof, especially its hydrochloride; the (3-endo)-8-methyl-8-azabicyclo[3.2.1]oct-3-yl ester of 1H-indole-3-carboxylic acid (3-tropanylindole-3-carboxylate, tropisetron) and pharmaceutically acceptable salts and solvates thereof, especially its hydrochloride, disclosed in U.S. Pat. No. 4,789,673; and 5-chloro-2,2-dimethyl-N-(8-methyl-8-azabicyclo[3.2.1]oct-3-yl)-2,3-dihydro-1-benzofuran-7-carboxamide (zatosetron) and pharmaceutically acceptable salts and solvates thereof, especially its maleate, disclosed in U.S. Pat. No. 5,563,148; the disclosures of all the US patents cited in this paragraph being incorporated herein in their entirety for reference.

Illustrative examples of pharmaceutically acceptable salts of said 5HT3-antagonists include addition salts with inorganic or organic acids such as hydrochloric acid, hydrobromic acid, sulfuric acid, sulfamic acid, phosphoric acid, nitric acid, acetic acid, propionic acid, stearic acid, glycolic acid, oxalic acid, succinic acid, lactic acid, maleic acid, hydroxymaleic acid, fumaric acid, malic acid, tartaric acid, citric acid, ascorbic acid, phenylacetic acid, glutamic acid, benzoic acid, salicylic acid, 2-acetoxybenzoic acid, methanesulfonic acid, ethanesulfonic acid, 2-hydroxyethanesulfonic (isethionic) acid, p-toluenesulfonic acid, 2-naphthalenesulfonic acid, 4-amino-benzenesulfonic (sulfanilic) acid, 2,6-naphthalenedisulfonic acid, 1,5-naphthalenedisulfonic acid, and pamoic (embonic) acid. Said salt may be solvated with a solvent, said solvent normally being water.

Antagonists of the 5HT3 receptor that are approved for the prevention or treatment of chemotherapy-induced nausea and vomiting are particularly useful according to the present invention. In particular, azasetron hydrochloride, commercially available in 10-mg tablets; dolasetron monomethanesulfonate monohydrate (also referred to as dolasetron mesylate), commercially available in 200-mg maximal dose tablet; granisetron hydrochloride, commercially available in 2.24-mg maximal dose tablet; ondansetron hydrochloride dihydrate, commercially available in 10-mg maximal dose (equivalent to 8 mg ondansetron base) tablet, and in a 2 mg/ml (in ondansetron base) solution available as a 20-ml multidose vial; palonosetron hydrochloride, commercially available in 0.56-mg tablets, and in 0.075 mg/1.5 ml or 0.25 mg/5 ml (in palonosetron base) vials; and tropisetron hydrochloride, commercially available in 5.64-mg capsules and in 2.265 mg-vial (corresponding to 2 mg of tropisetron base); are the preferred 5HT3-antagonists.

For the treatment of symptoms of muscle weakness associated with MG or other myasthenic disorders by oral route, the 5HT3-antagonist is administered at a single dose of from 0.001 mg/kg to 1.8 mg/kg of body weight, given from one to three times per day, with a maximum of 300 mg/day.

According to the present invention, the 5HT3-antagonist is used in a pharmaceutical or veterinary composition comprising, as an active ingredient, said 5HT3-antagonist in an amount per unit form of from 1 mcg to 300 mg.

Thus, for example, a pharmaceutical composition according to the present invention to be chronically administered in combination with pyridostigmine, may comprise a 5HT3-antagonist selected from the group consisting of azasetron and pharmaceutically acceptable salts and solvates thereof, in an amount per unit form equivalent to from 5 mg to 10 mg of azasetron hydrochloride, to be administered at a daily dose equivalent to from 15 mg to 40 mg of azasetron hydrochloride; dolasetron and pharmaceutically acceptable salts and solvates thereof, in an amount per unit form equivalent to from 25 mg to 200 mg of dolasetron mesylate, to be administered at a daily dose equivalent to from 75 mg to 200 mg of dolasetron mesylate; granisetron and pharmaceutically acceptable salts and solvates thereof, in an amount per unit form equivalent to from 0.5 mg to 2 mg granisetron base, to be administered at a daily dose equivalent to from 1.5 mg to 8 mg of granisetron base; ondansetron and pharmaceutically acceptable salts and solvates thereof, in an amount per unit form equivalent to from 2 mg to 16 mg, normally from 2 mg to 8 mg of ondansetron base, to be administered at a daily dose equivalent to from 6 mg to 64 mg, normally from 6 mg to 32 mg of ondansetron base; palonosetron and pharmaceutically acceptable salts and solvates thereof, in an amount per unit form equivalent to from 0.25 mg to 0.5 mg of palonosetron base, to be administered at a daily dose equivalent to from 0.75 to 2 mg of palonosetron base; and tropisetron and pharmaceutically acceptable salts and solvates thereof, in an amount per unit form equivalent to from 2.5 mg to 5 mg of tropisetron base, to be administered at a daily dose equivalent to from 7.5 mg to 20 mg of tropisetron base.

In the case of pediatric or obese patients, or also in the case of mammals such as cats and dogs, the daily dose may be decided on the basis of the body weight. Thus, for example, azasetron hydrochloride may be administered at a daily dose (in kg of body weight) of 0.4-0.5 mg/kg, dolasetron mesylate may be administered at a daily dose of 1.8 mg/kg, up to a maximum dose of 100 mg, normally of 9-9.5 mg/kg, granisetron hydrochloride may be administered at a daily dose of 0.09-0.11 mg/kg, ondansetron hydrochloride dihydrate may be administered at a daily dose of 0.45-0.55 mg/kg, palonosetron hydrochloride may be administered at a daily dose of 0.03 mg/kg and tropisetron hydrochloride may be administered at a daily dose of 0.5-0.6 mg/kg.

More particularly, in pediatric patients the normal single ondansetron hydrochloride dihydrate oral doses (in ondansetron base and in kg of body weight) are from 0.3 mg to 0.5 mg/kg, given every three hours, for neonates and infants, 0.9 mg/kg for a 3-kg baby; of 4 mg for a 8-15 kg child; from 6 mg to 8 mg for a 15-30 kg child; and the same as for adults and children weighing more than 30 kg.

Pyridostigmine

Pyridostigmine bromide is currently used for the oral treatment of patients suffering from MG, in particular in 60-mg tablets for IR administration, in 60 mg per 5 ml syrup, and in ER-unit forms containing 90 mg of pyridostigmine bromide.

According to the FDA approved label for pyridostigmine, in order to have a more complete response to the pyridostigmine treatment, high pyridostigmine doses should be administered, up to 1500 mg/day, using the 60 mg IR-tablets, or up to 1080 mg/day, using the 180 mg ER-tablets, possibly accompanied by supplemental IR-tablets. However, as set forth above, said doses are not tolerated in most patients. Higher doses than the currently recommended doses might provide further improvement and even a near-to-complete response, i.e., the complete alleviation of symptoms.

According to the present invention, by constantly combining (by concurrent administration) pyridostigmine bromide with a 5HT3-antagonist, said treatment becomes safe, and very high, fully effective doses are attained without appreciable adverse effects, thus improving the patients' conditions.

In addition, the present invention also allows the treatment of other mammals, in particular cats and dogs.

Normally, according to the present invention pyridostigmine is administered at a single dose calculated on the body weight of such mammals and administered to said mammals in a unit form comprising or delivering said pyridostigmine in predetermined amount.

In particular, pyridostigmine is administered to such mammals at a single dose, including titration doses, equivalent to from 0.05 mg/kg to 6 mg/kg of body weight of pyridostigmine bromide, in an unit form comprising or delivering a pyridostigmine amount equivalent to from 2 mg to 800 mg of pyridostigmine bromide.

For example, pyridostigmine is administered to a mammal at a single oral dose equivalent to from 0.5 mg/kg to 6 mg/kg of body weight of pyridostigmine bromide, given in unit forms comprising or delivering an amount per unit form equivalent to from 2 mg to 800 mg, said unit form being administered from 3-times/day to six 6-times/day.

Pyridostigmine may also be administered to such mammals at a single dose equivalent to from 0.1 mg/kg to 1.2 mg/kg of body weight of pyridostigmine bromide, given in unit forms for subcutaneous administration comprising an amount per unit form equivalent to from 0.4 mg to 200 mg of pyridostigmine bromide, said unit form being administered once or twice per day.

Thus, for example, an effective oral daily dose from 180 mg to 2400 mg (in the severe forms of the disease, from 1650 mg to 2400 mg and even more) normally from 180 mg to 1200 mg, in pyridostigmine bromide, may be safely administered to a patient suffering from MG or other myasthenic syndrome.

Appropriate unit forms consisting of a pharmaceutical or veterinary composition comprising a pharmaceutically acceptable salt of pyridostigmine, in an amount per unit form equivalent to from 0.4 mg to 800 mg, normally from 15 mg to 800 mg or from 30 mg to 800 mg of pyridostigmine bromide are provided by the present invention. These, to be safely administered for the treatment MG or other myasthenic syndromes, constantly and concurrently in combination with a 5HT3-antagonist.

A safer administration is assured by combining, in the same unit form, a 5HT3-antagonist, in an amount per unit form of from 1 mcg to 300 mg; and pyridostigmine, in an amount per unit form equivalent to from 0.4 mg to 800 mg, normally from 15 mg to 800 mg of pyridostigmine bromide.

Preferably, said 5HT3-antagonist is one of the approved 5HT3-antgonists illustrated in "The 5HT3-antagonist" section, in an amount per unit form as illustrated in the same section and said pyridostigmine is pyridostigmine bromide.

First Aspects of the Invention

According to a first aspect, the present invention provides a method for safely improving the conditions of a mammal, in particular a human being or another mammal such as a cat or a dog, suffering from symptoms of muscle weakness associated with MG or another myasthenic syndrome, by chronically administering to said mammal a 5HT3-antagonist in constant combination with pyridostigmine.

More particularly, the present invention proposes a method to safely improve the conditions or symptoms of muscle weakness of patients suffering from MG or another myasthenic syndrome, and treated with pyridostigmine by chronically administering to said patients a 5HT3-antagonist. More particularly, the present invention provides a method for treating symptoms of muscle weakness associated with MG and other myasthenic syndromes, which comprises administering to a patient in need of said treatment an effective daily dose of a 5HT3-antagonist in combination with an effective daily dose of pyridostigmine.

In carrying out the method of the present invention, the daily dose of these 5HT3-antagonists is at least as high as that preventing or treating nausea and vomiting in pediatric or adult patients under cancer chemotherapy according to the current protocols for said treatment. In particular, said daily dose is from 1 µg to 300 mg.

Normally, in the treatment of symptoms of muscle weakness associated with MG and other myasthenic disorders in a mammalian subject, and in particular, humans, dogs, and cats, (a) the 5HT3-antagonist is administered to said mammalian subject at a single oral or subcutaneous dose of from 0.001 mg/kg to 1.8 mg/kg of body weight, given from one to three times per day, with a maximum of 300 mg/day; and (b) pyridostigmine is administered to said mammalian subject: either at a single oral dose equivalent to from 0.5 mg/kg to 6 mg/kg of body weight of pyridostigmine bromide, given in unit forms comprising an amount per unit form equivalent to from 2 mg to 800 mg of pyridostigmine bromide, said unit form being administered from three times per day to six times per day; or at a single subcutaneous dose equivalent to from 0.1 mg/kg to 1.2 mg/kg of body weight of pyridostigmine bromide, said subcutaneous dose being in an unit forms comprising a pyridostigmine amount equivalent to from 0.4 mg to 200 mg of pyridostigmine bromide, said unit form being administered from once or twice per day.

Preferably, a human patient suffering from symptoms of muscle weakness associated with MG or other myasthenic disorders is treated with a 5HT3-antagonist selected from the group consisting of azasetron and pharmaceutically acceptable salts and solvates thereof, especially its hydrochloride, at a daily dose equivalent to from 15 mg to 20 mg of azasetron hydrochloride; dolasetron and pharmaceutically acceptable salts and solvates thereof, especially its mesylate monohydrate, at a daily dose equivalent to from 75 mg to 200 mg of dolasetron mesylate; granisetron and pharmaceutically acceptable salts and solvates thereof, especially its hydrochloride, at a daily dose equivalent to from 1.5 mg to 8 mg of granisetron base; ondansetron and pharmaceutically acceptable salts and solvates thereof, especially its hydrochloride dihydrate, at a daily dose equivalent to from 6 mg to 32 mg of ondansetron base; palonosetron and pharmaceutically acceptable salts and solvates thereof, especially its hydrochloride, at a daily dose equivalent to from 0.1 mg to 2 mg, preferably from 0.25 mg to 0.5 mg of palonosetron base; ramosetron and pharmaceutically acceptable salts and solvates thereof, especially its hydrochloride, at a daily dose equivalent to from 75 mcg to 100 mcg of ramosetron hydrochloride; and tropisetron and pharmaceutically acceptable salts and solvates thereof, especially its hydrochloride, at a daily dose equivalent to from 7.5 mg to 20 mg of tropisetron base.

The above daily dose of the above 5HT3-antagonist allows the safe administration of high pyridostigmine daily doses.

More particularly, the above daily doses of the above 5HT3-antagonist allow the safe administration of pyridostigmine fully effective doses equivalent to from 1080 mg/day to 2400 mg/day, from 1200 mg/day to 2400 mg/day or from more than 1500 mg/day to 2400 mg/day, and even more, of pyridostigmine bromide to a patient suffering from symptoms of muscle weakness associated with MG or other myasthenic syndromes.

Among the above 5HT3-antagonist to be used in combination, including fixed-dose combinations, with pyridostigmine, ondansetron and pharmaceutically acceptable salts or solvate thereof, dolasetron and pharmaceutically acceptable salts or solvates thereof, palonosetron and pharmaceutically acceptable salts or solvates thereof, ramosetron and pharmaceutically acceptable salts or solvates thereof, and tropisetron and pharmaceutically acceptable salts thereof are particularly advantageous.

Second Aspect of the Invention

According to a second aspect, the invention provides a 5HT3-antagonist for use in the treatment of symptoms of muscle weakness associated with MG and other myasthenic syndromes in combination with pyridostigmine.

Any 5HT3-antagonist, in particular those that are shown to be effective for the prevention or treatment of chemotherapy-induced nausea and vomiting may be used, in a combination, for example in a fixed-dose combination, with pyridostigmine according to this aspect of the present invention. Preferably, said 5HT3-antagonists are those approved for the prevention or treatment of chemotherapy-induced nausea and vomiting.

In particular, the 5HT3-antagonist is administered to a mammalian subject at a single oral or subcutaneous dose of from 0.001 mg/kg to 1.8 mg/kg of body weight, given from one to three times per day, with a maximum of 300 mg/day.

For said treatment, said 5HT3-antagonist single dose is formulated in a pharmaceutical composition in dosage unit form comprising an effective amount per unit form of said 5HT3-antagonist, in admixture with a pharmaceutical carrier or vehicle.

The amounts per unit form of said 5HT3-antagonists and the daily doses to be administered to a mammal such as a cat or a dog, or a human patient suffering from symptoms of muscle weakness associated with MG or another myasthenic syndrome in combination with pyridostigmine are illustrated in "The 5HT3-antagonist" section. More particularly said 5HT3-antagonist in said composition is selected from the group consisting of azasetron and pharmaceutically acceptable salts and solvates thereof, in an amount per unit form equivalent to from 5 mg to 10 mg of azasetron hydrochloride, to be administered at a daily dose equivalent to from 15 mg to 40 mg of azasetron hydrochloride; dolasetron and pharmaceutically acceptable salts and solvates thereof, in an amount per unit form equivalent to from 25 mg to 200 mg of dolasetron mesylate, to be administered at a daily dose equivalent to from 75 mg to 200 mg of dolasetron mesylate; granisetron and pharmaceutically acceptable salts and solvates thereof, in an amount per unit form equivalent to from 0.5 mg to 2 mg granisetron base, to be administered at a daily dose equivalent to from 1.5 mg to 8 mg of granisetron base; ondansetron and pharmaceutically acceptable salts and solvates thereof, in an amount per unit form equivalent to from 2 mg to 16 mg, normally from 2 mg to 8 mg of ondansetron base, to be administered at a daily dose equivalent to from 6 mg to 64 mg, normally from 6 mg to 32 mg of ondansetron base; palonosetron and pharmaceutically acceptable salts and solvates thereof, in an amount per unit form equivalent to from 0.25 mg to 0.5 mg of palonosetron base, to be administered at a daily dose equivalent to from 0.75 to 2 mg of palonosetron base; and tropisetron and pharmaceutically acceptable salts and solvates thereof, in an amount per unit form equivalent to from 2.5 mg to 5 mg of tropisetron base, to be administered at a daily dose equivalent to from 7.5 mg to 20 mg of tropisetron base, and is for use for the treatment of symptoms of muscle weakness associated with MG and other myasthenic syndromes, in combination with a pyridostigmine pharmaceutically acceptable salt.

Ondansetron and pharmaceutically acceptable salts and solvates thereof, dolasetron and pharmaceutically acceptable salts and solvates thereof, palonosetron and pharmaceutically acceptable salts and solvates thereof, ramosetron and pharmaceutically acceptable salts and solvates thereof, and tropisetron and pharmaceutically acceptable salts thereof are particularly preferred in said composition.

Said composition allows a safe treatment of symptoms of muscle weakness associated with MG and other myasthenic syndromes, in combination with pyridostigmine. In said combination, pyridostigmine may be administered to mammalian subjects at a single oral dose equivalent to from 0.5 mg/kg to 6 mg/kg of body weight of pyridostigmine bromide. Said single dose is formulated in a unit form comprising an amount of from 2 mg to 800 mg of pyridostigmine bromide, said unit form being administered from three times per day to six times per day.

Said composition also allows the administration of a single subcutaneous dose equivalent to from 0.1 mg/kg to 1.2 mg/kg of body weight of pyridostigmine bromide, said subcutaneous dose being in an unit forms comprising a pyridostigmine amount equivalent to from 0.4 mg to 200 mg of pyridostigmine bromide, said unit form being administered once or twice per day.

In particular, said composition allows a safe treatment of a patient suffering from symptoms of muscle weakness associated with MG or other myasthenic syndrome, in combination with pyridostigmine oral daily doses equivalent to from 180 mg to 2400 mg (and even more), normally from 180 mg to 1500 mg, from 180 mg to 1200 mg, from 180 mg to 1080 mg or from 180 mg to 720 mg of pyridostigmine bromide.

More particularly, said composition allows the administration of pyridostigmine fully effective oral doses equivalent to from 1080 mg/day to 2400 mg/day, from 1200 mg/day to 2400 mg/day or from more than 1500 to 2400 mg/day, and even more, of pyridostigmine bromide to a human patient suffering from symptoms of muscle weakness associated with MG or other myasthenic syndromes.

Third Aspect of the Invention

According to a third aspect, the invention provides the use of a 5HT3-antagonist for the preparation of a medicament for the treatment of a mammal such as a cat or a dog, or a human patient suffering from symptoms of muscle weakness associated with MG or other myasthenic syndromes in combination with pyridostigmine.

Said 5HT3-antagonist is administered to said mammal at a single dose of from 0.001 mg/kg to 1.8 mg/kg of body weight, given from one to three times per day, with a maximum of 300 mg/day, in combination with pyridostigmine, administered to said mammal:
(a) either at a single oral dose equivalent to from 0.5 mg/kg to 6 mg/kg of body weight of pyridostigmine bromide, given in unit forms comprising an amount per unit form equivalent to from 15 mg to 800 mg of pyridostigmine bromide, said unit form being administered from three times per day to six times per day; or
(b) at a single subcutaneous dose equivalent to from 0.1 mg/kg to 1.2 mg/kg of body weight of pyridostigmine bromide, said subcutaneous dose being in an unit forms comprising a pyridostigmine amount equivalent to from 0.4 mg to 200 mg of pyridostigmine bromide, said unit form being administered from once or twice per day.

For use in the treatment of symptoms of muscle weakness associated with MG and other myasthenic syndromes in said combination with pyridostigmine, the 5HT3-antagonist is formulated in a pharmaceutical or veterinary composition wherein said 5HT3-antagonist is in admixture with a pharmaceutical carrier or vehicle.

In certain preferred embodiments, the present invention provides pharmaceutical compositions including, as one of their active ingredients, a pharmacologically active amount of a 5HT3-antagonist as shown above or of one of its pharmaceutically acceptable salts, in mixture with a pharmaceutical carrier or vehicle.

In the pharmaceutical compositions of the present invention for oral, subcutaneous, intravenous, transdermal or topical administration, the 5HT3-antagonist active ingredient is preferably administered, in the form of dosage units and in mixture with the classic pharmaceutical carriers or vehicles, in combination with pyridostigmine.

The posology can vary widely depending on the age, weight, and the health condition of the patient. This posology includes the administration of a dose of from 1 mcg to 300 mg of a particular 5HT3-antagonist according to the potency of each type of 5HT3-antagonist and the age of the patient, from one to three times a day by intravenous, subcutaneous, oral, or transcutaneous administration.

The pharmaceutical compositions of the present invention are formulated with the classic excipients suitable for different ways of administration. Particularly advantageous are the formulations in the form of tablets, multi-score tablets, coated tables, orally disintegrating tablets, extended release tablets, hard or soft capsules, extended-release capsules, patches for transdermal administration, liquid oral solutions, syrups or suspensions in a predetermined unit form, and vials for intravenous or subcutaneous administration.

The aforementioned pharmaceutical composition comprising said 5HT3-antagonist, at the aforesaid amounts per unit form, is administered to a patient suffering from MG or another myasthenic syndrome in combination with pyridostigmine, also in a pharmaceutical composition in dosage unit form, comprising an amount per adult or pediatric unit form equivalent to from 0.4 mg to 800 mg, normally from 15 mg to 800 mg, from 30 mg to 800 mg, from 30 mg to 400 mg, from 30 mg to 360 mg, from 30 mg to 270 mg, or from 30 mg to 240 mg of pyridostigmine bromide, in admixture with a pharmaceutical carrier or vehicle.

In said combination, the amount of pyridostigmine per pediatric or adult unit form, will advantageously be equivalent to a range of from 0.4 mg to 800 mg, normally from 15 mg to 800 mg, from 30 mg to 800, from 30 mg to 600 mg. from 30 mg to 400 mg, from 30 mg to 200 mg, from 30 mg to 180 mg or from 30 mg to 90 mg, of pyridostigmine bromide, depending on safety and tolerability (per day the dose is equivalent to a range of from 30 mg to 2400 mg (from 1650 mg-2400 mg and even more in severe MG forms), normally from 30 mg to 1200 mg, from 30 mg to 1080 mg or from 30 mg to 720 mg of pyridostigmine bromide).

More particularly, in said combination, the above daily doses of the above 5HT3-antagonist allow the administration of pyridostigmine fully effective doses equivalent to from 1080 mg/day to 2400 mg/day, from 1200 mg/day to 2400 mg/day or from more than 1500 to 2400 mg/day, and even more, of pyridostigmine bromide to a human patient suffering from symptoms of muscle weakness associated with MG or other myasthenic syndromes.

Ondansetron and pharmaceutically acceptable salts and solvates thereof, dolasetron and pharmaceutically acceptable salts and solvates thereof, palonosetron and pharmaceutically acceptable salts and solvates thereof, ramosetron and pharmaceutically acceptable salts and solvates thereof, and tropisetron and pharmaceutically acceptable salts thereof are particularly preferred in said composition.

If the 5HT3-antagonist is ondansetron, the dose per tablet, to be administered to a patient in combination with pyridostigmine, will range from 2 mg to 16 mg, normally from 2 mg to 8 mg or from 4 mg to 8 mg.

The amount per unit form of pyridostigmine in an ER-formulation, to be administered to an adult patient, will be equivalent to a range consisting of from 90 mg to 800 mg, normally from 90 mg to 500 mg, from 90 mg to 400 mg, from 90 mg to 360 mg, from 90 mg to 270 mg, and from 90 to 240 mg of pyridostigmine bromide per tablet administered 3 times per day. If the 5-HT3 antagonist is dolasetron, the dose per tablet in combination with pyridostigmine will range from 100 mg to 200 mg of dolasetron. If the 5HT3-antagonist is palonosetron hydrochloride in an IR-formulation, the dose per tablet to be used in combination with pyridostigmine is equivalent to from 0.25 mg to 0.5 mg of palonosetron base. Said tablet is destined to be administered once a day or once every two days.

Preferably, said pyridostigmine is pyridostigmine bromide.

Ondansetron may also be present in a composition for transdermal administration, subcutaneous administration, intravenous administration, in a slow-release composition, such as extended release tablets or capsules, or a combination product, for example as a Transdermal Drug Delivery System (TDDS) such as a patch, preferably a matrix patch like that described by Cho J-R et al 2016; a patch pump, an infusion pump, or a micropump; or a fast-dissolving buccal film such as that described by Koland M et al. 2013.

"Transdermal drug delivery system" provides transdermal delivery using transdermal drug formulations and transdermal patches incorporating such transdermal drug formulations. For example, the transdermal drug delivery system may include a composition in form of a patch, a cream, a gel, a lotion, or a paste comprising a 5HT3-antagonist (such as ondansetron). Examples of transdermal formulations may include, but are not limited to, those as described in U.S. Pat. No. 6,562,368, a transdermal gel formulation as described in U.S. Pat. Nos. 7,029,694; 7,179,483; 8,241,662 and US 2009/0018190, a transdermal or transmucosal pharmaceutical formulation, that can be utilized for topical or transdermal application, such that solutions, creams, lotions, sprays, ointment, gels, aerosols and patch drug deliveries as described in WO 2005/039531, US 2007/022379, US 2010/0216880, US 2014/0037713 and U.S. Pat. No. 8,652,491, a transdermal absorption preparation as described in WO2013/061969 and US 2014/0271796, the disclosures of which are herein incorporated by reference in their entirety. The transdermal patches may also include, but are not limited to, a patch pump having an in-dwelling rigid catheter with flexible features and/or a flexible catheter attachment as described in U.S. Pat. No. 9,782,536, a selectively activatable patch pump as described in U.S. Pat. No. 9,724,462, a patch pump attached to a wireless communication system as described in U.S. Pat. No. 9,623,173, a conformable patch pump as described in U.S. Pat. No. 9,616,171, an infusion pump as described in U.S. Pat. No. 8,915,879, a portable infusion drug delivery as described in U.S. Pat. No. 8,480,649, a micropump as described in U.S. Pat. No. 8,282,366, and a patch pump as described in U.S. Pat. No. 7,828,771; the disclosures of which are herein incorporated by reference in their entirety. Other transdermal patches may include, but are not limited to, a patch in which oxybutynin is incorporated in an adhesive agent layer composition comprises the acrylic-based polymer as the adhesive base agent, and the acrylic-based polymer is a copolymer of polymethyl methacrylate with a polyacrylateas described in U.S. Pat. No. 8,802,134, a patch consisting of a support layer and of an adhesive agent layer arranged on the at least one surface of the support layer as described in U.S. Pat. No. 8,877,235, a patch using a monoglyceride or a mixture of monoglycerides of fatty acids as skin permeation-enhancer as described in U.S. Pat. Nos. 5,441,740 and 5,500,222, a patch for using a monoglyceride or a mixture of monoglycerides plus a lactate ester as skin permeation-enhancer as described in U.S. Pat. Nos. 5,686,097; 5,747,065; 5,750,137 and 5,900,250, a patch with a non-rate controlling tie layer on the skin-proximal surface of the reservoir, not affecting the drug release as described in U.S. Pat. Nos. 5,614,211 and 5,635,203, a patch using triacetin as permeation enhancer as described in U.S. Pat. Nos. 5,212,199, 5,227,169, 5,601,839 and 5,834,010, a patch with a matrix mass in the form of a layer which is self-adhesive, and in which the matrix mass consists of ammonium-group-containing (meth)acrylate copolymers as described in U.S. Pat. No. 6,555,129, a transdermal patch as described in U.S. Pat. Nos. 6,743,441; 7,081,249; 7,081,250; 7,081,251; 7,081,252 and 7,087,241; the disclosures of which are herein incorporated by reference in their entirety. Preferably, the transdermal drug delivery system is a patch, a patch pump, an infusion pump, or a micropump.

In the treatment of symptoms of muscle weakness associated with MG and other myasthenic syndromes, the 5HT3-antagonist and the pyridostigmine are used in combination and the two active components may be co-administered simultaneously or sequentially, or in a fixed dose combination including a pharmaceutical composition comprising the 5HT3-antagonist and pyridostigmine, in admixture with a pharmaceutically acceptable carrier or vehicle.

The 5HT3-antagonist Component (a) and the pyridostigmine Component (b) can be administered separately or together in any conventional oral or parenteral dosage unit form such as capsule, tablet, powder, cachet, suspension, solution, or transdermal device. The amount of 5HT3-antagonist per unit form in preferred embodiments will be in the range of from 1 μg to 300 mg. The amount of pyridostigmine per unit form in preferred embodiments will be in the range of from 30 mg to 400 mg, normally from 30 mg to 240 mg.

In the case of separate (concurrent or sequential) administration of said 5HT3-antagonist, in an effective amount per unit form, and of said pyridostigmine, in an effective amount per unit form, each of them can be packaged in a kit comprising said 5HT3-antagonist, in admixture with a pharmaceutical carrier or vehicle, in a container; and said pyridostigmine, in admixture with a pharmaceutical carrier or vehicle, in another, separate container.

For the concurrent administration of said 5HT3-antagonist and of said pyridostigmine, the two active principles can be formulated together and with a pharmaceutical carrier or vehicle, in a pharmaceutical or veterinary composition.

Accordingly, the present invention provides the use of a 5-HT3 antagonist for the preparation of a medicament for the treatment of symptoms of muscle weakness associated with MG and other myasthenic syndromes in combination with pyridostigmine, said medicament including a pharmaceutical composition in dosage unit form comprising said 5HT3-antagonist and said pyridostigmine pharmaceutically acceptable salt, in admixture with a pharmaceutical carrier or vehicle.

Fourth Aspect of the Invention

According to a fourth aspect of the present invention, the pharmaceutical composition comprising a 5HT3-antagonist may contain another active ingredient, in particular pyridostigmine, co-formulated with said 5HT3-antagonist, in admixture with a pharmaceutical carrier or vehicle.

Thus, the present invention further provides a fixed-dose combination including a pharmaceutical or veterinary composition in dosage unit form comprising, as active ingredients, Component (a) a 5HT3-antagonist; and Component (b) pyridostigmine, in admixture with a pharmaceutical carrier or vehicle.

Normally, in said composition, the 5HT3-antagonist Component (a) is present in an amount per unit form of from 1 μg to 300 mg and the pyridostigmine Component (b) is present in an amount equivalent to of from 0.4 mg to 800 mg, normally to from 15 mg to 800 mg, or from 30 mg to 800 mg of pyridostigmine bromide.

Said fixed-dose combination is useful for the treatment of MG and other myasthenic disorders in a mammal such as a cat, a dog, or a human being. Said treatment safely provides said mammal with a 5HT3-antagonist dose of from 1 mcg to 300 mg and a single pyridostigmine dose equivalent to from 0.4 mg to 800 mg of pyridostigmine bromide.

If said mammal is a human being, the above fixed-dose combination may be safely used for the treatment of infants, including neonates, and also includes pyridostigmine doses for the titration.

According to an embodiment,
- (a) said 5HT3-antagonist Component (a) active ingredient is selected from the group consisting of azasetron and pharmaceutically acceptable salts and solvates thereof, in an amount per unit form equivalent to from 5 mg to 10 mg of azasetron hydrochloride; dolasetron and pharmaceutically acceptable salts and solvates thereof, in an amount per unit form equivalent to from 25 mg to 200 mg of dolasetron mesylate; granisetron and pharmaceutically acceptable salts and solvates thereof, in an amount per unit form equivalent to from 0.5 mg to 2 mg of granisetron base; ondansetron and pharmaceutically acceptable salts and solvates thereof, in an amount per unit form equivalent to from 2 mg to 16 mg, preferably from 2 mg to 8 mg of ondansetron base; palonosetron and pharmaceutically acceptable salts and solvates thereof, in an amount per unit form equivalent to from 0.25 mg to 0.5 mg of palonosetron base; and tropisetron and pharmaceutically acceptable salts and solvates thereof, in an amount per unit form equivalent to from 2.5 mg to 5 mg of tropisetron base; and
- (b) said pyridostigmine pharmaceutically acceptable salt Component (b) is in an amount per unit form equivalent to a range selected from the group consisting of from 15 mg to 800 mg, from 30 mg to 800 mg, from 30 mg to 600 mg, from 30 mg to 400 mg, from 30 mg to 360 mg, from 30 mg to 270 mg, from 30 mg to 240 mg, from 30 mg to 180 mg and from 30 mg to 90 mg of pyridostigmine bromide; and
- (c) the Components are mixed together and with a pharmaceutical carrier or vehicle.

In particular, according to this embodiment,
- (a) said 5HT3-antagonist Component (a) is selected from the group consisting of azasetron hydrochloride, in an amount per unit form of from 5 mg to 10 mg; dolasetron mesylate, in an amount per unit form of from 25 mg to 200 mg; granisetron hydrochloride, in an amount per unit form equivalent to from 0.5 mg to 2 mg granisetron base; ondansetron hydrochloride dihydrate, in an amount per unit form equivalent to from 2 mg to 8 mg of ondansetron base; palonosetron hydrochloride, in an amount per unit form equivalent to from 0.25 mg to 0.5 mg of palonosetron base; and tropisetron hydrochloride, in an amount per unit form equivalent to from 2.5 mg to 5 mg of tropisetron base; and
- (b) said pharmaceutically acceptable salt of pyridostigmine is pyridostigmine bromide, in an amount per unit form of from 15 mg to 800 mg, from 30 mg to 800 mg, from 30 mg to 600 mg, from 30 mg to 400 mg, or from 30 mg to 240 mg.

In the above 5HT3-antagonist/pyridostigmine fixed dose combinations, the above-illustrated pharmaceutical compositions in dosage unit form are preferably administered to a pediatric or adult patient suffering from symptoms of muscle weakness associated with MG or another myasthenic syndrome to provide a pyridostigmine daily dose equivalent to from 30 mg to 2400 mg, and even more, normally from 270 mg to 1500 mg (up to 1650-2250 mg in severe forms), from 270 mg to 1200 mg, from 270 mg to 1080 mg or from 270 mg to 720 mg of pyridostigmine bromide.

As set forth above, the pharmaceutical compositions are formulated in admixture with a pharmaceutical carrier or vehicle for any administration route. For example, said pharmaceutical compositions are in a pharmaceutical dosage unit form for oral, intravenous, intramuscular, intranasal, intraperitoneal, subcutaneous, transdermal, or rectal administration.

The pharmaceutical compositions may be formulated in oral forms such as tablets or gelatin capsules wherein the 5HT3-antagonist or pyridostigmine or both the active ingredients are in admixture with a carrier or vehicle that may include a diluent, such as cellulose, dextrose, lactose, mannitol, sorbitol or sucrose; a lubricant, such as, acid, calcium or magnesium stearate, polyethylene glycol, silica, or talc; and if needed, a binder such as magnesium aluminum silicate, gelatin, methylcellulose, sodium carboxymethylcellulose, or polyvinylpyrrolidone.

Said oral forms may be tablets coated with sucrose or with various polymers; or, alternatively, the tablets can be manufactured by using carriers such as acrylic and methacrylic acid polymers and copolymers; cellulose derivatives such as hydroxypropylethylcellulose; or other appropriate materials, to have a prolonged or delayed activity by progressively releasing a predetermined quantity of 5HT3-antagonist or of pyridostigmine, or of both the active ingredients. The oral formulations can also be in form of capsules allowing the extended release of the 5HT3-antagonist, or of pyridostigmine, or of both the active ingredients.

The unit forms may be formulated in tablets in which Component (a) or Component (b) or both of the two components is in Extended Release ("ER")-formulation, for example in admixture with hydroxypropyl methyl cellulose or in a film-coated microgranule. Carriers and vehicles for ER tablets include retardant materials such as acrylic and methacrylic acid polymers and copolymers; the aforementioned cellulose derivatives such as hydroxypropylmethylcellulose, hydroxyethyl cellulose, hydroxypropyl ethylcellulose, hydroxypropyl cellulose, methylcellulose, ethylcellulose, or sodium carboxymethylcellulose; gums; waxes; glycerides or aliphatic alcohols or a mixture thereof.

When the 5HT3-antagonist and pyridostigmine are in a fixed-dose combination, the unit form may be a stratified, bi-layer tablet wherein the 5HT3-antagonist, formulated with a pharmaceutical carrier, is in one of the layers and pyridostigmine, formulated with a pharmaceutical carrier, is the other layer. Similarly, the 5HT3-antagonist and pyridostigmine active ingredients are in a pill containing one of the active ingredients, admixed with a pharmaceutical carrier, in the core and the other active ingredient, admixed with a pharmaceutical carrier, is in the outer part of the pill, the core and the outer part being optionally separated by an inert film or carrier. Analogously, capsules made of two separated parts, one containing Component (a), in IR- or ER-formulation and the other containing Component (b), in IR- or ER-formulation, may be manufactured.

The fixed-dose combinations may also be pharmaceutical compositions formulated as an orally disintegrable tablet wherein Component (a) and Component (b) are mixed together and with a hydrophobic agent and a diluent to form a fast release composition which efficiently delivers said components orally, for example as disclosed, for ondansetron Component (a) alone, in GB 1548022, GB 2111423, GB 2119246, GB 2114440, GB 2111184, GB 2120370, and U.S. Pat. No. 5,046,618 U.S. Pat. Nos. 5,188,825, 5,955,488, 7,390,503 and in WO 2004/096214, the contents of which are incorporated herein in their entirety for reference and for pyridostigmine Component (b) alone, in WO 2006/005017, the contents of which are incorporated herein in their entirety by reference.

An useful pharmaceutical composition according to the present invention is formulated in a liquid formulation, such, as a syrup, wherein Component (a) and Component (b) are dissolved in admixture with a pharmaceutical carrier, for example, for ondansetron Component (a) alone, as described in U.S. Pat. No. 5,854,270, the contents of which are incorporated herein in their entirety for reference and, for pyridostigmine Component (b) alone, as in its commercially available liquid formulation.

Said compositions in the form of orally disintegrable tablets or syrups may also comprise sweeteners, lubricants, taste-masking agents, binders, coloring agents and, in the case of orally disintegrable tablets, salivation stimulants.

A typically orally disintegrable tablet will contain an amount of ondansetron hydrochloride dihydrate equivalent to from 2 mg 16 mg of ondansetron base, preferably an amount of ondansetron hydrochloride dihydrate equivalent to 4 mg, 6 mg or 8 mg of ondansetron base, as Component (a); and 800 mg, normally 400 mg or 200 mg, of pyridostigmine bromide, as Component (b).

A typical syrup will contain an amount of from 2 mg/5 ml to 8 mg/5 ml of ondansetron base or an amount of ondansetron hydrochloride dihydrate Component (a) equivalent to from 2 mg/ml to 8 mg/ml of ondansetron base; and from 30 mg/5 ml to 60 mg/5 ml of pyridostigmine bromide Component (b).

A syrup for pediatric patients will comprise an amount of ondansetron hydrochloride dihydrate Component (a) equivalent to from 0.5 mg/ml to 2 mg/ml of ondansetron base and an amount of from 2 mg/ml to 15 mg/ml of pyridostigmine bromide.

The pharmaceutical compositions may also be formulated in a transdermal drug delivery system (TDDS), such as a patch formulation wherein the active ingredient or the mixture of the active ingredients may comprise adjuvants such as D-sorbitol, gelatin, kaolin, methyl paraben, polysorbate 80, propylene glycol, propyl paraben, povidone, sodium carboxymethylcellulose, sodium polyacrylate, tartaric acid, titanium dioxide, and purified water. A patch formulation may also contain skin permeability enhancer such as lactate esters such as lauryl lactate, triacetin or diethylene glycol monoethyl ether.

In embodiments of the above pharmaceutical compositions, a preferred 5HT3-antagonist Component (a) active ingredient is selected from the group consisting of ondansetron base, ondansetron hydrochloride dihydrate, palonosetron base, palonosetron hydrochloride, dolasetron base, and dolasetron mesylate monohydrate; and the preferred pharmaceutically acceptable salt of pyridostigmine is pyridostigmine bromide. Each of these active ingredients is present in said compositions in the amount per unit form illustrated herein above.

According to an embodiment, the compositions of the present invention are formulated by mixing Component (a) and Component (b) together, in admixture with a pharmaceutical carrier for an immediate release. An advantageous composition according to this embodiment comprises ondansetron hydrochloride dihydrate, in an amount equivalent to from 2 mg to 8 mg of ondansetron base, as Component (a); and 800 mg of pyridostigmine bromide, as component (b). Components (a) and (b) are mixed together and with a pharmaceutical carrier in an IR- or ER-formulation. Said composition is destined to be administered from one to three times per day.

Another composition according to this embodiment comprises ondansetron hydrochloride dihydrate, in an amount equivalent to from 2 mg to 4 mg of ondansetron base, as Component (a); and 400 mg of pyridostigmine bromide, as Component (b). Components (a) and (b) are mixed together and with a pharmaceutical carrier in an IR-formulation. This composition may be administered from two to four times per day.

Example 1

The ability of 5HT3-antagonists to prevent the gastro-intestinal adverse effects of pyridostigmine bromide in humans was tested.

A Phase I study was conducted in human subjects receiving a single oral dose of pyridostigmine bromide with or without a single oral dose of ondansetron hydrochloride dihydrate ("ondansetron"), as a representative 5HT3-antagonist. The study was a single center, single-blind study.

The objective of the study was to demonstrate that ondansetron could safely attenuate the gastro-intestinal adverse effects of pyridostigmine given in doses shown to be effective for the treatment of MG (Mestinon® Prescribing Information).

To be enrolled in the study, participants had to meet the following inclusion/exclusion criteria:
Key Inclusion Criteria
 1. Healthy male or female volunteers between the ages of 18 and 50 years inclusive.
 2. Females of childbearing potential were required to agree to be abstinent or else use any two of the following medically acceptable forms of contraception from the Screening Period through 14 days after the study Exit Visit: hormonal contraception, condom with spermicidal jelly, diaphragm or cervical cap with spermicidal jelly, or IUD. A female whose male partner had had a vasectomy was required to agree to use one additional form of medically acceptable contraception. Subjects were required agree to practice the above birth control methods for 14 days after the final visit as a safety precaution.
 3. Females of non-childbearing potential, defined as surgically sterile (status post hysterectomy, bilateral oophorectomy, or bilateral tubal ligation) or post-menopausal for at least 12 months, did not require contraception during the study. Post-menopausal had to be confirmed by a serum FSH test at Screening and the reason must be documented in the source documents.
 4. Subjects had to be in good health as determined by their medical history including personal and family psychiatric history, physical examination, ECG, vital signs, and laboratory tests. A subject with a medical abnormality could be included only if the investigator or designee considered that the abnormality would not introduce significant additional risk to the subject's health or interfere with study objectives.

5. Subjects had to have a body mass index between 19 and 30 kg/m² (both inclusive).

6. Subjects were required to have signed an informed consent form indicating that they understood the purpose of and procedures required for the study and were willing to participate in the study and comply with the study procedures and restrictions.

Subjects had to be able to swallow multiple pills simultaneously.

Key Exclusion Criteria:

1. The criteria for exclusion of a subject from enrollment in the study were as follows:

2. Any clinically relevant acute or chronic diseases, including mechanical intestinal or urinary obstruction and bronchial asthma, which could interfere with the subjects' safety during the trial, expose them to undue risk, or interfere with the study objectives.

3. History or presence of gastrointestinal, hepatic, or renal disease or other condition known to interfere with the absorption, distribution, metabolism, or excretion of drugs.

4. History of substance abuse, known drug addiction, or positive test for drugs of abuse or alcohol.

5. Current use of potent CYP 3A4 inhibitors or apomorphine (contraindication for use of ondansetron).

6. History or presence of myasthenia gravis.

7. History of drug or another significant allergy.

8. Known hypersensitivity to pyridostigmine or other carbamates, or to ondansetron or similar serotonin receptor antagonists.

9. History of and/or current QT interval prolongation and congenital long QT syndrome. Electrolyte abnormalities (e.g., hypokalemia or hypomagnesemia), congestive heart failure, bradyarrhythmias or other medicinal products that lead to QT prolongation.

10. Treatment with centrally active drugs or those affecting peripheral cholinergic transmission within 3 months of study entry.

11. Current or Former Smokers (except subjects who stopped smoking 1 year or more before enrollment in the Study) including tobacco products.

12. Excessive daily consumption of xanthines containing drinks (i.e. >500 mg/day of caffeine).

13. Subjects unwilling to curtail prolonged intensive physical exercise during the study conduct (from the Screening visit until the last dose of study drug).

14. Positive test result for hepatitis B surface antigen, hepatitis C antibody.

15. Positive test result for HIV 1 and 2 serology.

16. Likely to need any medical or dental treatment during the study period.

17. Use of any prescription or over-the-counter medication within 14 days prior to admission on Day-1. In addition, any medications with central effects are prohibited for a period equal to 5 times the drug half-life prior to admission (Day-1), should this period be longer than 14 days.

18. Subjects unlikely to co-operate during the study, and/or be questionably compliant in the opinion of the investigator.

19. Subjects unable to be contacted in case of an emergency.

20. Intake of an investigational drug within 30 days of study entry.

Following enrollment in the study, participants received single increasing oral doses of pyridostigmine, given once daily in the morning. The starting dose of pyridostigmine was 30 mg and the dose was increased daily by 30 mg increments. Once a subject had reached his/her first intolerable dose ("FID-1"), upward dose escalation was discontinued. FID was defined as:

(a) One (1) episode of vomiting, or
(b) Two (2) episodes of retching, or
(c) One (1) episode of severe nausea (Grade 3; defined as nausea interfering with activities of daily living or inadequate oral caloric or fluid intake; tube feeding, total parenteral nutrition or hospitalization indicated) lasting more than 1 hour, or
(d) Three (3) consecutive episodes at every 4-hour ratings of moderate nausea (Grade 2; defined as subjectively symptomatic, but not interfering with activities of daily living), or
(e) One (1) episode of moderate diarrhea (Grade 2; defined as 4-6 stools more than at baseline).

When a subject reached FID-1 on pyridostigmine alone, the subject was washed out for 2 to 7 days, and then received single daily doses of pyridostigmine starting at 30 mg and titrated upward by 30 mg increments, together with oral ondansetron hydrochloride dihydrate (10 mg, equivalent to 8 mg ondansetron base) until subjects again reached an intolerable dose (FID-2).

On each study day, subjects were followed up for up to 8 hours following drug administration for AEs, vital signs, ECGs. In addition, a laboratory panel was taken at screening and at the end of the study.

Three subjects were enrolled in the study. The following table summarizes the demographic characteristics of the subjects.

Demographic Characteristics of Subjects Enrolled in the Study

| Subject ID | Gender | Age (years) | Baseline Weight (kg) |
| --- | --- | --- | --- |
| 004/106 | Male | 43 | 82.3 |
| 030/104 | Male | 34 | 90.9 |
| 027/108 | Female | 40 | 72.2 |

All subjects reached FID-1 (pyridostigmine alone) during the study. The dose limiting toxicity was vomiting in all 3 subjects. No subject reached FID-2 (pyridostigmine with ondansetron) and all subjects tolerated the maximum pyridostigmine dose allowed by the protocol of 120 mg. In other words, concomitant administration of ondansetron with pyridostigmine prevented the occurrence of gastro-intestinal adverse events. The following Table lists for each subject the values for FID-1 (on pyridostigmine alone) and FID-2 (on pyridostigmine+ondansetron).

Listing of First Intolerable Doses (FID) Values

| Subject ID | FID-1 (Pyridostigmine alone) | FID-1 Dose Limiting Adverse Event | FID-2 Pyridostigmine + Ondansetron |
| --- | --- | --- | --- |
| 004/106 | 60 mg | Vomiting | Not reached |
| 030/104 | 60 mg | Vomiting | Not reached |
| 027/108 | 90 mg | Vomiting | Not reached |

As shown in the following table, the MTD-2 was increased by more than 4-times in 2 subjects and by more than 2-times in one subject.

Listing of Maximum Tolerated Doses (MTD)

| Subject ID | MTD-1 (Pyridostigmine alone) | Maximal Tolerated Dose Pyridostigmine + Ondansetron | MTD2/ MTD1 |
|---|---|---|---|
| 004/106 | 30 mg | >120 mg | >4 |
| 030/104 | 30 mg | >120 mg | >4 |
| 027/108 | 60 mg | >120 mg | >2 |

MTD: Maximum Tolerated Dose

Taken together, results showed that the co-administration of ondansetron with pyridostigmine attenuated GI AEs reported with pyridostigmine alone, thus showing that a 5HT3-antagonist enables the administration to a human being of a pyridostigmine dose otherwise non-tolerated when administering pyridostigmine alone.

In conclusion, the co-administration of oral high dose ondansetron with pyridostigmine prevented the occurrence of GI AEs associated with pyridostigmine given in doses at least as high as or much higher than the currently recommended efficacious dose for the symptomatic treatment of MG, thus indicating the possibility of enabling full efficacy of pyridostigmine by administering doses higher than, for example, the maximum currently recommended ER-pyridostigmine daily dose of approximately 900 to 1,120 mg to a patient suffering from MG or another myasthenic syndrome.

Example 2

Immediate release tablets for oral administration are prepared using 3 kg of pyridostigmine bromide, 0.5 kg of ondansetron hydrochloride dihydrate, 2.5 kg of silicon dioxide, 13.6 kg of lactose, 6 kg of corn starch, 1.3 kg of pregelatinized maize starch, and 0.1 kg of magnesium stearate. The active ingredients are sieved through a suitable sieve and blended with silicon dioxide, lactose, starch, and pregelatinized maize starch. Suitable volumes of purified water are added and the powders are granulated. After drying, the granules are screened and blended with the magnesium stearate. The granules are then compressed, using a conventional tableting machine, into 100,000 tablets, each weighing 270 mg, having the following composition:

| | |
|---|---|
| Pyridostigmine bromide | 30 mg |
| Ondansetron HCl•2H$_2$O | 5 mg |
| Silicon dioxide | 25 mg |
| Lactose | 136 mg |
| Corn Starch | 60 mg |
| Pregelatinized maize starch | 13 mg |
| Magnesium stearate | 1 mg |

Example 3

By operating as described in Example 2, by using 0.25 kg of ondansetron hydrochloride dihydrate instead of 0.5 kg, and 10.5 mg of pregelatinized maize starch, instead of 13 mg, immediate release tablets for oral administration weighing 265 mg containing an amount of ondansetron hydrochloride dihydrate equivalent to 2 mg of ondansetron base are obtained.

Example 4

By operating as described in Example 2, by using 20 kg of pyridostigmine bromide 10 mg of ondansetron hydrochloride dihydrate, 3 kg of silicon dioxide, 11 kg of lactose, 4 kg of corn starch and 0.9 kg of pregelatinized maize starch, and 0.1 mg of magnesium stearate, immediate release tablets for oral administration weighing 400 mg containing 200 mg of pyridostigmine bromide and an amount of ondansetron hydrochloride dihydrate equivalent to 8 mg of ondansetron base are prepared.

Example 5

Capsules containing 30 mg of pyridostigmine bromide, 5 mg of ondansetron hydrochloride dihydrate, 64 mg of corn starch and 1 mg of magnesium stearate are manufactured. The active ingredients, previously mixed in a mixer, are sieved and blended with the excipients. The mixture thus obtained is then filled into size No. 2 hard gelatin capsules using conventional machine.

The foregoing detailed description has been given for illustration purposes only, especially for purposes of clarity of understanding. It will be apparent to those skilled in the art that certain changes and modifications may be practiced without departing from the spirit and scope of the invention, which is delineated by the appended claims.

REFERENCES

1. Abicht A, Muller J S, Lochmüller H. Congenital Myasthenic Syndromes. In: Pagon R A, Adam M P, Ardinger H H, Wallace S E, Amemiya A, Bean L J H, Bird T D, Ledbetter N, Mefford H C, Smith R J H, Stephens K, editors. GeneReviews®[Internet]. Seattle (Wash.): University of Washington, Seattle; 1993-2016. 2003 May 9 [updated 2016 Jul. 14].
2. Cho J-R et al 2016: Cho J-R, Duong A V, Nguyen L I T, Chi S-C. "Design of transdermal matrix patch containing ondansetron". J Pharm Investigation. 2016 46(7): 677-684.
3. Drachman D B. Myasthenia Gravis. Semin Neurol. 2016; 36:419-424. Epub 2016 Sep. 23.
4. Engel A G. Congenital Myasthenic Syndromes in 2012. Curr. Neurol Neurosci Rep, 2012; 12:92-101.
5. Gotterer L, Li Y. Maintenance immunosuppression in myasthenia gravis. J Neurol 20 Sci. 2016; 369:294-302. Epub 2016 Aug. 28.
6. Howard J. F. Clinical Overview of MG. Myasthenia Gravis Foundation of America; 2015.
7. Koland J V I et al. 2010: Koland M, Sandeep V P. Charyulu N R. "Ondansetron Hydrochloride: Effect of Additives on in vitro Drug Release and Mucosal Permeation. J Young Pharmacists. 2010, 2(3):216-222.
8. O'Grady G L, Verschuuren C, Yuen M, Webster R, Menezes M, Fock J M, Pride N, Best H A, Benavides Damm T, Turner C, Lek M, Engel A G, North K N, Clarke N F, MacArthur D G, Kamsteeg E J, Cooper S T. Variants in SLC18A3, vesicular acetylcholine transporter, cause congenital myasthenic syndrome. Neurology. 2016; 87:1442-1448. Epub 2016 Sep. 2.
9. Phillips W D I, Vincent A2. Pathogenesis of myasthenia gravis: update on disease types, models, and mechanisms. FI000Res. 2016; 27:5.
10. Shelton G D I. Myasthenia gravis and congenital myasthenic syndromes in dogs and cats: A history and mini-review. Neuromuscul Disord. 2016; 26: 331-334. Epub 2016 Mar. 10.
11. Smith S V, Lee A G. Update on Ocular Myasthenia Gravis. Neurol Clin. 2017; 35:115-123.

The invention claimed is:

1. A fixed-dose combination product for administration to a mammal comprising a pharmaceutical composition in dosage unit form comprising as active ingredients (a) between 2 mg and 16 mg of a 5HT3-antagonist and (b) between 15 mg and 800 mg of pyridostigmine, which are (c) in admixture with a pharmaceutically acceptable carrier or vehicle.

2. The fixed-dose combination product of claim 1, wherein the pyridostigmine is pyridostigmine bromide.

3. The fixed-dose combination product of claim 2, wherein the 5HT3-antagonist is an ondansetron 5HT3-antagonist comprising ondansetron or a pharmaceutically acceptable salt or solvate thereof.

4. The fixed-dose combination product of claim 3, wherein the product is an immediate release formulation.

5. The fixed-dose combination product of claim 3, wherein the product is an extended release formulation.

* * * * *